United States Patent [19]

Hawman

[11] 4,419,763
[45] Dec. 6, 1983

[54] VARIABLE SLANTED CHANNEL COLLIMATOR

[75] Inventor: Eric G. Hawman, Buffalo Grove, Ill.

[73] Assignee: Siemens Gammasonics, Inc., Des Plaines, Ill.

[21] Appl. No.: 269,423

[22] Filed: Jun. 1, 1981

[51] Int. Cl.³ .............................................. G21F 5/04
[52] U.S. Cl. ..................................... 378/149; 378/150
[58] Field of Search ............... 378/147, 149, 150, 151, 378/152, 153

[56] References Cited

U.S. PATENT DOCUMENTS

| | | | |
|---|---|---|---|
| 2,139,966 | 12/1938 | Loebell | 378/149 |
| 2,405,444 | 8/1946 | Moreau | 378/159 |
| 2,659,017 | 11/1953 | Bartow | 378/149 |
| 3,790,782 | 2/1974 | Inoue | 378/149 |
| 3,997,794 | 12/1976 | York | 378/149 |
| 4,143,273 | 3/1979 | Richey | 378/150 |
| 4,181,839 | 1/1980 | Hatton | 378/149 |

Primary Examiner—Craig E. Church
Attorney, Agent, or Firm—Karl F. Milde, Jr.

[57] ABSTRACT

A collimator is disclosed which has a stack of radiation opaque plates that is tilted to vary the angle of view of the scintillation crystal of a radiation detector with respect to a radiation source. The plates have hexagonal apertures that are aligned with corresponding apertures on adjacent plates to provide radiation transmitting channels. As the stack is tilted, the plates slide laterally over one another to change the slant of the channels.

8 Claims, 7 Drawing Figures

VARIABLE SLANTED CHANNEL COLLIMATOR

BACKGROUND OF THE INVENTION

1. Field of the Invention

This invention relates to a collimator for a radiation detecting device such as a scintillation camera used for medical diagnoses.

2. Description of the Prior Art

Radiation collimators are used in radiation detecting devices for channeling radiation between a source of radiation and a radiation sensitive transducer. An example of a radiation detecting device to which the present invention finds application is the Anger-type scintillation camera, the basic principles of which are explained in U.S. Pat. No. 3,011,057. The Anger camera is a nuclear radiation detecting device which is widely used in the medical field for analyzing the distribution of a gamma radiation emitting substance in a human body organ. The purpose of using a collimator with a radiation detecting device is to define radiation transmitting channels between a source of radiation (e.g. a human body organ) and a transducer (e.g. a scintillation crystal of an Anger camera) so that radiation emitted from spatial areas of the radiation source can be mapped to corresponding spatial areas of the transducer. The most commonly used collimator is the multi-channel collimator which comprises a number of radiation transmitting apertures or channels separated from each other by radiation opaque walls or septa.

Most collimators for gamma ray cameras are of a unitary construction. When they are mounted on the camera head, the viewing angle of the head with respect to the source of radiation is fixed. For many clinical studies, however, it is desirable to vary the aspect angle of the image of view. This can be done by moving the camera. This may, however, lead to degradation of the resolution of the image. For example, where the camera head is rotated when a parallel hole collimator is used, some parts of the collimator face may be at a greater distance from the patient (or organ of interest) than others which distorts the picture. To overcome such a problem, a variety of slanted channel collimators have been developed. Nevertheless, when a change in the viewing angle is desired, it cannot be done without repositioning the camera head or changing the collimator.

SUMMARY OF THE INVENTION

It is an object of the present invention to provide a slanted channel collimator in which the angle of slant can be selectively varied to change the angle of view of a radiation detector with respect to a source of radiation without repositioning the camera head and without changing the collimator.

It is another object of this invention to provide a stereo collimator which can selectively vary the angles of view of a radiation detector as to a plurality of images of a source of radiation.

In accordance with one aspect of the invention, a variable slanted channel collimator is provided for selectively varying the angle of view of a radiation detector with respect to a radiation source which comprises a plurality of radiation opaque plates, each formed with a multiplicity of apertures. The respective plates are so positioned with respect to one another that corresponding apertures of adjacent plates are aligned to provide slanted radiation transmitting apertures or channels. Means are provided for moving the plates relative to each other for changing the degree of slant of the channels thereby changing the angle of view of the detector.

In a preferred embodiment described in detail below, apertured plates are arranged one on top of another in a stack. The degree of slant of the channels is varied by means which tilt the stack so that the plates shift or slide laterally with respect to each other. Framing members positioned peripherally of the stack provide stability and ease of tilting.

In another aspect of the invention, a stereo collimator is provided which has two sets of apertured plates. The respective plates of each set have aligned corresponding apertures to define slanted channels and are relatively moveable to change the degree of slant, thereby providing two selectively variable simultaneous angles of view of the detector.

There have thus been outlined rather broadly certain objects, features and advantages of the invention in order that the detailed description that follows may be better understood, and in order that the present contribution to the art may be better appreciated. There are, of course, additional features of the invention that will be described more fully hereinafter. Those skilled in the art will appreciate that the conception on which this disclosure is based may readily be utilized as the basis for the designing of other arrangements for carrying out the purposes of this invention. It is important, therefore, that this disclosure be regarded as including all such equivalent arrangements that encompass the spirit and scope of the invention.

BRIEF DESCRIPTION OF THE DRAWINGS

Embodiments of the invention have been chosen for the purposes of illustration and description, and are shown in the accompanying drawings forming a part of the specification, wherein.

Like elements are referred to by like numerals throughout the drawings.

DESCRIPTION OF THE PREFERRED EMBODIMENT

Figure 1:
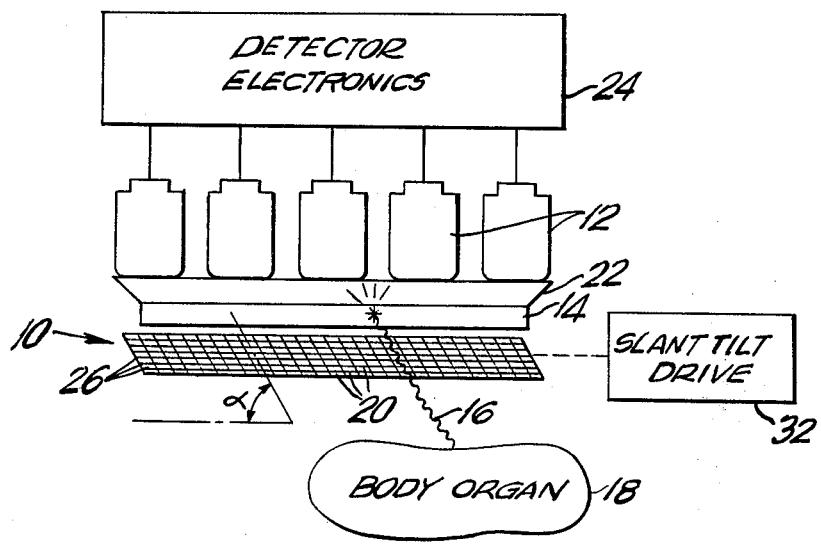
FIG. 1 is a schematic view of an Anger camera system employing a collimator in accordance with an embodiment of the present invention.

FIGS. 1–4 show a preferred collimator 10 as used with an Anger-type scintillation camera. The Anger-type camera has a scintillation detector head (FIG. 1) in which a hexagonal array of 19 or 37 photomultiplier tubes 12 view overlapping portions of a scintillation crystal 14 which is formed in the shape of a disc. A gamma ray 16 emitted from a body organ 18 is transmitted through the slanted channels 20 of the collimator 10 disposed at an angle $\alpha$ with respect to the face of the crystal 14 and impinges upon the crystal 14. The ray 16 hitting the crystal 14 causes flashes of light to be emitted which travel through light pipe 22 and are detected by photomultiplier tubes 12 viewing the area of emission. The photomultiplier tubes 12 generate electrical signals proportional to the magnitude of the light intensity received. These signals are transmitted to the detector electronics 24 where they are matrixed together to provide positional information to identify the point of origin of the scintillation in the plane of the crystal 14.

The collimator 10 is interposed between the radiation source 18 and the detector crystal 14 so that the location of the scintillation will correspond to the point of origin in the body organ 18 of the incident gamma ray 16 causing scintillation. This point is then depicted in a two-dimensional matrix for use in diagnostic analysis.

The collimator 10 comprises a plurality of apertured plates 26, each formed with a multiplicity of closely packed hexagonal apertures 28. The apertured plates 26 are positioned within a collimator housing 30 (FIG. 3) so that corresponding apertures 28 of adjacent plates 26 align to provide a plurality of parallel radiation transmitting paths or channels 20 slanted at an angle $\alpha$ (FIGS. 1,3,4, and 5A) with respect to the front planar surface of the disc-shaped scintillation crystal 14. The plates 26 are positioned one on top of another to form a stack and a tilt drive mechanism 32 serves to tilt the stack in order to move the plates 26 laterally relative to one another, thereby realigning the apertures 28 to provide radiation transmitting channels 20' (see FIG. 5B) of other slant angles, thereby varying the angle of view of the radiation detecting crystal 14 with respect to the radiation source 18.

Figure 5A:
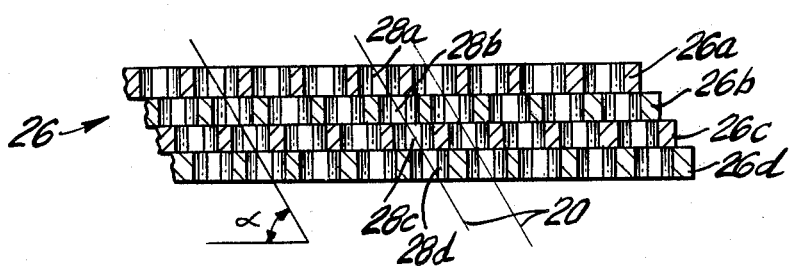
FIGS. 5A and 5B are schematic representations useful in understanding the principles of the operation of the collimator of FIG. 1.
Figure 5B:
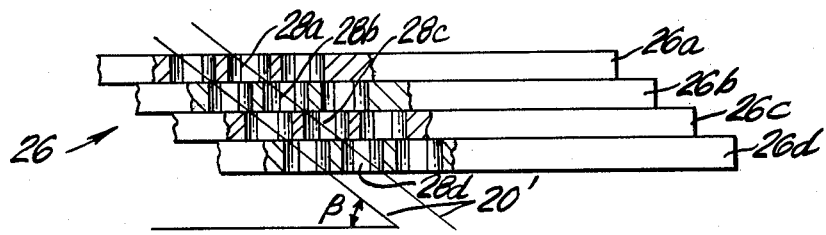

The change in the slant angle of the radiation transmitting channels 20 of the collimator 10 caused by relative lateral shifting of the apertured plates 26 with respect to each other is illustrated in FIGS. 5A and 5B. FIG. 5A shows the stack of plates 26 relatively positioned so that corresponding apertures 28a, 28b, 28c and 28d of adjacent plates 26a, 26b, 26c and 26d provide slanted radiation transmitting channels 20 having an angle $\alpha$ with respect to the face of crystal 14. FIG. 5B shows the plates 26 relatively positioned to provide slanted channels 20' having an angle $\beta$ with respect to the face of crystal 14. The plates 26 positioned as shown in FIGS. 5A and 5B correspond respectively to angles of view $\alpha$ and $\beta$ of the Anger camera with respect to the body organ 18 (see FIG. 1).

Figure 2:
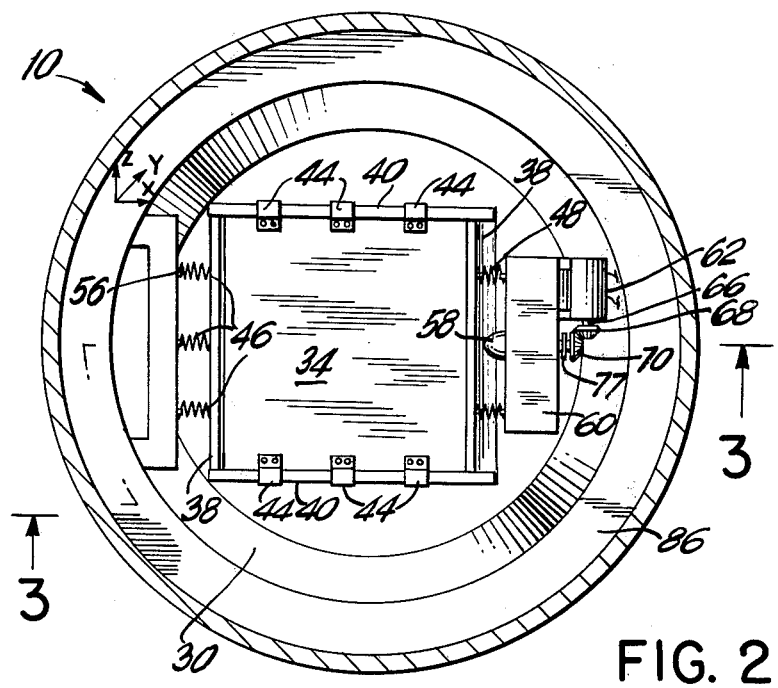
FIG. 2 is a top plan view of the collimator of FIG. 1.
Figure 3:
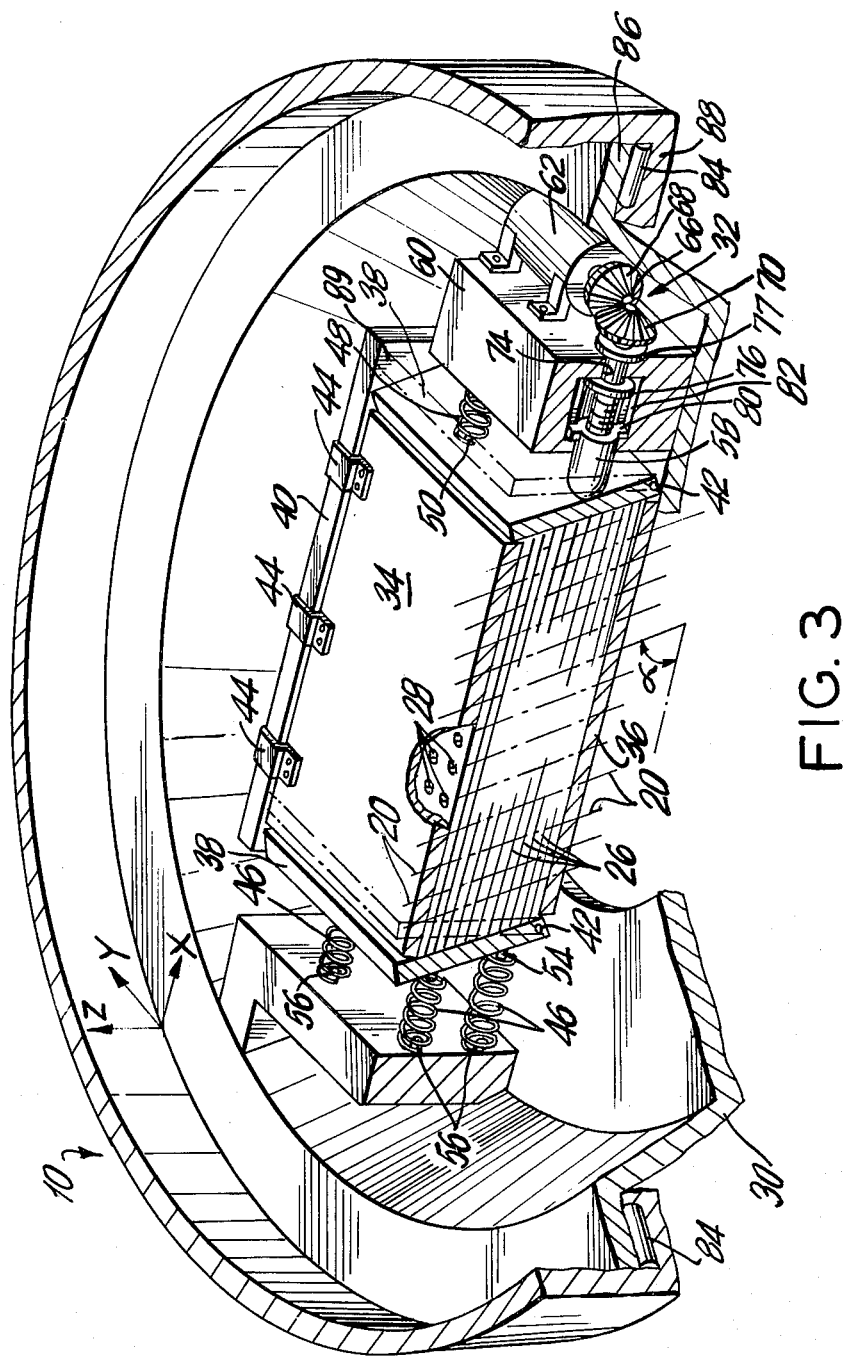
FIG. 3 is a perspective section view taken along the lines 3—3 of FIG. 2.
Figure 4:
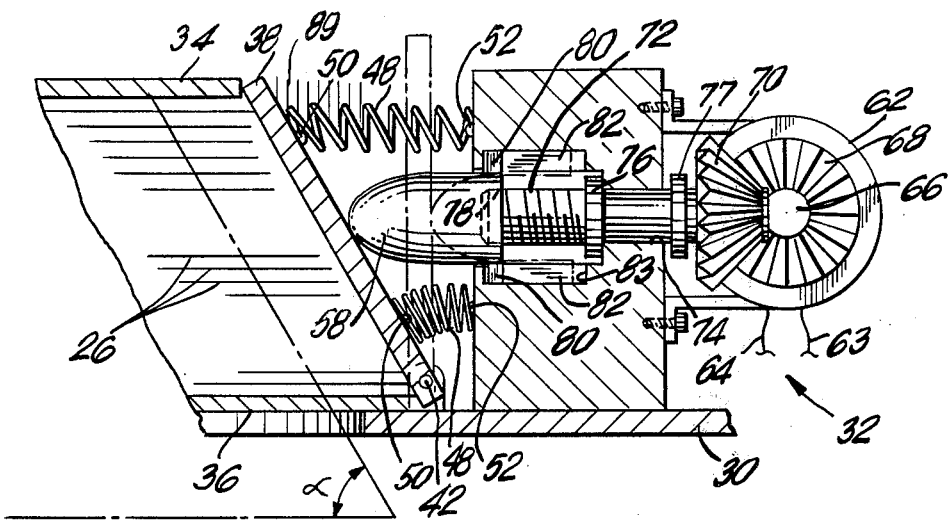
FIG. 4 is an enlarged side elevation view of part of FIG. 2.

FIGS. 2-4 show the details of construction of the variable slanted channel collimator 10. The apertured plates 26 comprise identical thin rectangular sheets of radiation opaque material, such as lead or tungsten, each formed with a closely packed uniform distribution of hexagonal apertures 28. The plates 26 are stacked in the configuration of a parallelepiped with the exposed surfaces framed by six rectangular framing members: a cover plate 34 at the top, a base plate 36 at the base, two tipper members 38 abutting the right and left sides and two keeper members 40 abutting the front and rear sides (see FIGS. 2 and 3).

The cover plate 34 and base plate 36 are nonapertured and made of radiation transmitting material, such as aluminum. The plates 34 and 36 are relatively thick compared to the apertured plates 26. The base plate 36 and the two keeper members 40 are fixedly supported with respect to the housing 30. The right and left tipper members 38 are both mounted for pivotal movement on the housing 30 about hinges 42. The stack cover plate 34 is positioned between the upper edges of the tipper members 38 and the upper edges of the keeper plates 40.

Several spring-loaded bearings 44 are mounted on the keeper members 40 to exert downward force against the cover plate 34 and the underlying stack in order to stabilize the stack during lateral shifting of the plates 26 and the cover plate 34. Two sets of springs 46 and 48 attached to anchors 50, 52 and 54, 56 serve to bias the right and left tipper members 38, respectively, into the vertical neutral positions shown by the dashed lines in FIGS. 3 and 4. This serves to bias the stack of apertured plates 26 into an upright untilted position.

Lateral movement of the plates 26 with respect to each other is effected by a pusher 58 which moves against the non-stack side of the right tipper member 38 to apply a force which tilts the right tipper member 38 about the hinge 42 from the neutral position (shown by dashed lines in FIGS. 3 and 4) to a tilted position (shown by solid lines in FIGS. 3 and 4). The tilting of the right tipper member 42 applies a tilting force to the stack of plates 26 which opposes the biasing force exerted by the sets of springs 46 and 48. The tilt drive mechanism 32 which includes the pusher 58 is mounted to the housing 30 at a mounting block 60. An electric motor 62 which is excited by electrical signals received on wires 63 and 64 is fastened to the outer surface of the block 60 and functions to rotate an output drive shaft 66. A bevel gear 68 mounted on the shaft 66 for rotation therewith meshes with a second bevel gear 70 mounted on another shaft 72 which extends at right angles to the shaft 66, through a bore 74 in the mounting block 60 and is held in place by shaft retainer bearings 76 and 77. The end of the shaft 12 which is opposite the second bevel gear 70 (the left end as seen in FIGS. 3 and 4) is externally threaded and engages matching internal threads of an end bore 78 of the pusher 58. The pusher 58 also has upper and lower keys 80 which extend into longitudinal key slots 82 located at the top and bottom of a cavity 83 formed in the mounting block 60. The cavity 83 accommodates the movement of the pusher 58 from the neutral position in which the stack of plates 26 is upright (shown by dashed lines in FIG. 4) to the advanced positions in which the stack of plates 26 is tilted (shown, for example, by the solid lines in FIG. 4).

In operation, when the pusher arm 58 is in the dashed position shown in FIG. 4, the stack is in an upright or neutral position. The angle $\alpha$ of the radiation transmitting channels 20 formed by the aligned apertures 28 of the plates 26 is 90° and the channels are vertical. An electrical impulse imparted to the motor 62 by wires 63, 64, causes the output shaft 66 to rotate and thus rotates the associated bevel gear 68. When the bevel gear 68 rotates, it causes rotation of the second bevel gear 70 which rotates the pusher drive shaft 72. The shaft 72 and pusher 58 cooperate in the manner of a lead screw and a screw thread follower so that the rotatory movement of the shaft 72 is translated into linear movement of the pusher 58. When the external threads at the free end of shaft 72 rotate within the end bore 78 of the pusher 58, the internal threads of the bore 78 drive the pusher 58 linearly against the right tipper member 38 to a stack tilting position, such as shown by the solid lines in FIG. 4. The keys 80 which travel in the longitudinal key slots 82 of the mounting block 60 inhibit rotation of the pusher 58, but allow the pusher 58 to move back and forth against the right tipper member 38.The leading end of the pusher 58 is rounded to that the point of contact of the pusher 58 with the outside surface of the right tipper plate 38 can change as the plate is tipped. The point of contact moves upward as the member 38 pivots away from the pusher 58. The springs 46 and 48 exert a force which opposes the force exerted by the pusher 58 against the right tipper member 38 and urge the stack of plates 26 to remain in an upright position.

As the right tipper member 38 is pivoted around its hinge pivot point 42, the plates 26 slide laterally across each other and the plate stack tilts from the neutral position (shown by the dashed lines in FIGS. 3 and 4) to a position in which the apertures 28 define slanted radiation transmitting channels. The base plate 36 does not move, nor do the keeper members 40. The plates 26 move horizontally with respect to the housing 30 and laterally with respect to each other. The plates 26 that are higher in the stack move a greater distance than the plates 26 which are lower in the stack. The movement of the plates 26 is in the x-axis direction as shown in FIG. 3. Movement in the y-axis direction (FIG. 3) is prevented by stationery keeper members 40. Movement in the z-axis direction (FIG. 3) is restrained by the fixed base plate 36 and the downward force exerted by the spring-loaded bearings 44 on the top of the cover plate 34.

The plates 26 are made thin (2 to 3 mm) and the stack of plates has on the order of 100 plates in it. Oil or grease which is radiation transmissive is spread between the plates 26 to give lubrication to aid in the sliding movement of one plate over another. Because the plates will slide over each other if lead is used as the radiation opaque material, it may be desirable to use a lead alloy or construct a laminar plate of lead and a more rigid material so that the softness of the lead will not interfere with the tilting operation.

Roller bearings 84 (FIG. 3) are positioned on the periphery of the collimator housing 30 between overlapping flanges 86 and 88 serve as means for rotating the stack of plates 26 with respect to the scintillation crystal 14. When the collimator 10 is in place on the detector head of the Anger camera (FIG. 1), the combination of the collimator rotation about its center vertical axis along the bearings 84 and the variation in slant angle of the channels brought about by selective pivoting of the right tipper member 38 by the tilt drive mechanism 32 provides great flexibility in changing the angle of view of the detector with respect to the radiation source.

An index, such as markings 89, scored into the surface of the rear keeper member 40 against which the top edge of the right tipper member 38 travels, provides a visual indication of the angle of view to which the collimator 10 is set (see FIG. 3).

Figure 6:
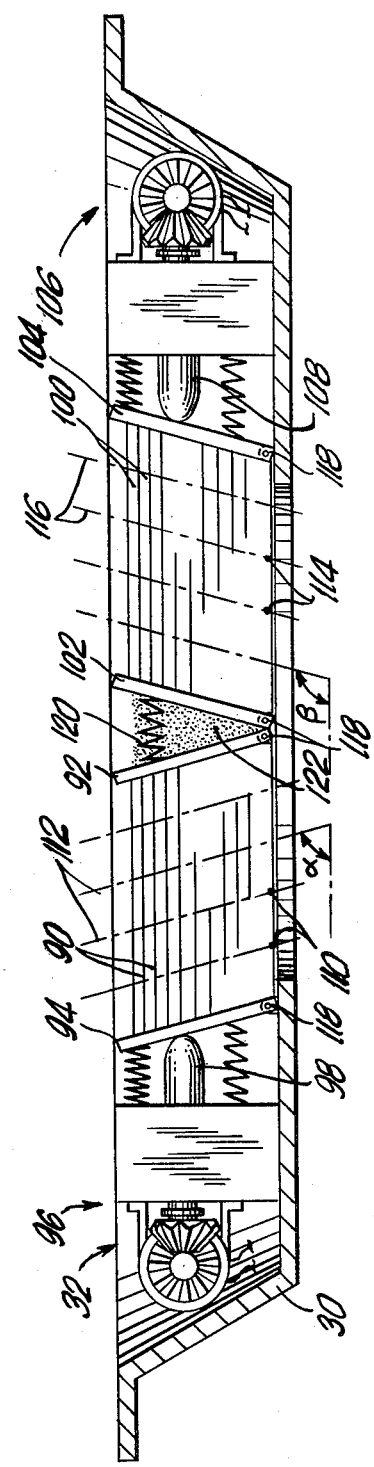
FIG. 6 is an elevation view in section of an alternative embodiment of the present invention, taken at a point similar to that of FIG. 3.

FIG. 6 illustrates another embodiment of the present invention in which a first stack of apertured plates 90 framed by pivoted framing members 92 and 94 (left side of FIG. 6) move laterally with respect to each other by means of a tilting mechanism 96 having a pusher 98; and apertured plates 100 framed by framing members 102 and 104 move laterally with respect to one another by means of a tilting mechanism 106 having a pusher 108. The apertures 110 of apertured plates 90 are aligned to define first radiation transmitting channels 112 which have a slant angle $\alpha$ with respect to the face of the scintillation crystal 14 (see also FIG. 1). The apertures 114 of the apertured plates 100 align to define second radiation transmitting channels 116 which have a slant angle $\beta$ with respect to the face of the scintillation crystal 14. The framing members 92 and 102 are pivotally connected to the collimator housing 30 at a common hinge 118 and biased into an open-V position by means of a spring 120. The pocket formed by the nonstack sides of the framing members 92 and 102 is lined with a plastic or other flexible material to hold lead powder 122 which prevents the transmission of radiation through the central region of the collimator that is not blocked as to radiation by the apertured plates 90 and 100. The tilting mechanisms 96 and 105 have elements identical to the elements of the tilting mechanism 32 described above in connection with the first embodiment. The collimator shown in FIG. 6 functions as a stero collimator (an example of which is disclosed in U.S. Pat. No. b 4,181,839) to permit dual simultaneous imaging of a body organ 18 at angles of view $\alpha$ and $\beta$.

Having thus described the invention with particular reference to the preferred forms of variable slanted channel collimators, it will be obvious to those skilled in the art to which the invention pertains, after understanding the invention, that various changes and modifications may be made therein without departing from the spirit and scope of the invention as defined by the claims appended hereto. Positional references of certain elements shown in the drawings (such as "left", "right", etc.) have been made throughout this specification merely to facilitate the explanation of the preferred embodiments, and such positional references should not be viewed as limiting the positions which such elements may have in other embodiments. Similarly, it will be appreciated that the dimensions, shapes and layout of the housing, plates, apertures, etc. may be v aried to suit individual tastes and requirements.

What is claimed is:

1. A collimator for selectively varying the angle of view of a radiation detector with respect to a radiation source, comprising
   a housing;
   a plurality of apertured plates of radiation opaque material positioned within the housing so that corresponding apertures of adjacent plates are aligned to provide slanted channels for the transmission of radiation; and
   means for moving the plates relative to one another to change the degree of slant of the channels thereby varying the angle of view of the detector.

2. A collimator as defined in claim 1, wherein the apertured plates are arranged one on top of another to form a stack; and wherein the means for moving the plates comprises means for tilting the stack so that the plates shift laterally relative to each other.

3. A collimator as defined in claim 2, further comprising framing members positioned within the housing peripherally of the stack to frame the stack and to provide stability to the stack during tilting.

4. A collimator as defined in claim 3, wherein the apertured plates are rectangular; the stack of plates has the shape of a parallelopiped having four sides, a base and a top; the framing members comprise two keeper members respectively positioned against two opposite sides of the stack and two tipper members respectively positioned against the remaining two sides of the stack; and wherein the means for tilting the stack comprises means for tilting one of the tipper members.

5. A collimator as defined in claim 4, further comprising means for biasing the stack of plates into the upright position.

6. A collimator as defined in claim 5, wherein the keeper members are fixedly mounted and the tipper members are pivotally mounted with respect to the housing; the biasing means comprises means for biasing the tipper members into a neutral position; and the tilting means comprises a pusher arm which moves against the non-stack side of said one tipper member to thereby apply a tilting force to the stack in opposite to the upright position biasing force.

7. A collimator as defined in claims 1, 2 or 6 in combination with a scintillation camera having a scintillation crystal mounted in a detector head, wherein the housing further comprises means for mounting the collimator on the detector head for rotation with respect to the scintillation crystal.

8. A collimator with a first plurality of apertured plates as defined in claim 1, further comprising a second plurality of apertured plates of radiation opaque material positioned within the housing so that corresponding apertures of adjacent ones of the second plurality of plates are aligned to provide other slanted channels for the transmission of radiation; and means for moving the second plurality of plates relative to one another to change the angle of slant of the second channels, thereby providing a stero collimator for selectively varying two simultaneous angles of view of the radiation detector with respect to the radiation source.

* * * * *